United States Patent
Miller et al.

(10) Patent No.: US 9,943,360 B2
(45) Date of Patent: Apr. 17, 2018

(54) COIL ELECTRODE FOR THERMAL THERAPY

(75) Inventors: Brock James Miller, Mahwah, NJ (US); Michael Sherar, Toronto (CA); Claire McCann, Toronto (CA); Michael Jewett, Toronto (CA); John R. Kachura, Toronto (CA); Alex Furse, Toronto (CA); Mark William Taylor, Etobicoke (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 168 days.

(21) Appl. No.: 13/982,337

(22) PCT Filed: Jan. 30, 2012

(86) PCT No.: PCT/CA2012/050053
§ 371 (c)(1),
(2), (4) Date: Oct. 10, 2013

(87) PCT Pub. No.: WO2012/100355
PCT Pub. Date: Aug. 2, 2012

(65) Prior Publication Data
US 2014/0296845 A1 Oct. 2, 2014

Related U.S. Application Data

(60) Provisional application No. 61/437,653, filed on Jan. 30, 2011.

(51) Int. Cl.
*A61B 18/12* (2006.01)
*A61B 18/14* (2006.01)
(Continued)

(52) U.S. Cl.
CPC ...... *A61B 18/1477* (2013.01); *A61B 18/1492* (2013.01); *A61B 17/3415* (2013.01);
(Continued)

(58) Field of Classification Search
CPC ............ A61B 17/3415; A61B 18/1447; A61B 18/1492; A61B 2018/00577;
(Continued)

(56) References Cited

U.S. PATENT DOCUMENTS

| 4,154,246 A | 5/1979 | LeVeen |
| 4,494,539 A | 1/1985 | Zenitani et al. |

(Continued)

FOREIGN PATENT DOCUMENTS

| DE | 69330947 T2 | 4/2002 |
| EP | 1092452 A2 | 4/2001 |

(Continued)

OTHER PUBLICATIONS

US 6,648,882, 11/2003, Behl et al. (withdrawn)
(Continued)

*Primary Examiner* — Daniel Fowler
(74) *Attorney, Agent, or Firm* — Bereskin & Parr LLP/S.E.N.C.R.L., s.r.l.; Tony Orsi

(57) ABSTRACT

A coil electrode for use with an RFA (radio frequency ablation) apparatus, has a lead portion, and a helical portion coupled to the lead portion, the helical portion being formed of Nitinol SE510. Further, an RFA (radio frequency ablation) apparatus, comprises an applicator, the applicator including a handle and a cannulating delivery needle mounted to the handle, the cannulating delivery needle including a tip spaced apart from the handle. A coil electrode includes a lead portion housed in the cannulating delivery needle, and a helical portion coupled to the lead portion, the helical portion formed of Nitinol. The helical portion has a retracted state when housed within the cannulating delivery needle and a deployed state when moved out of the tip of the cannulating delivery needle.

19 Claims, 8 Drawing Sheets

(51) Int. Cl.
  *A61B 17/34* (2006.01)
  *A61B 18/00* (2006.01)
  *A61B 34/20* (2016.01)

(52) U.S. Cl.
  CPC ..... *A61B 34/20* (2016.02); *A61B 2018/00577* (2013.01); *A61B 2018/1435* (2013.01); *A61B 2018/1475* (2013.01)

(58) Field of Classification Search
  CPC .... A61B 2018/1435; A61B 2018/1475; A61B 19/5244
  See application file for complete search history.

(56) References Cited

U.S. PATENT DOCUMENTS

| | | |
|---|---|---|
| 4,834,092 A | 5/1989 | Alexson et al. |
| 5,186,181 A | 2/1993 | Franconi et al. |
| 5,246,438 A | 9/1993 | Langberg |
| 5,300,099 A | 4/1994 | Rudie |
| 5,364,392 A | 11/1994 | Warner et al. |
| 5,413,588 A | 5/1995 | Rudie et al. |
| 5,419,777 A * | 5/1995 | Hofling ............... A61B 18/24 128/831 |
| 5,423,848 A * | 6/1995 | Washizuka et al. ......... 606/185 |
| 5,464,445 A | 11/1995 | Rudie et al. |
| 5,470,352 A | 11/1995 | Rappaport |
| 5,486,183 A * | 1/1996 | Middleman ........... A61B 10/02 606/113 |
| 5,507,743 A | 4/1996 | Edwards et al. |
| 5,536,267 A | 7/1996 | Edwards et al. |
| 5,545,137 A | 8/1996 | Rudie et al. |
| 5,672,173 A | 9/1997 | Gough et al. |
| 5,755,754 A | 5/1998 | Rudie et al. |
| 5,814,044 A | 9/1998 | Hooven |
| 5,817,092 A | 10/1998 | Behl |
| 5,871,523 A | 2/1999 | Fleischman et al. |
| 5,916,240 A | 6/1999 | Rudie et al. |
| 5,916,241 A | 6/1999 | Rudie et al. |
| 6,030,382 A | 2/2000 | Fleischman et al. |
| 6,050,992 A | 4/2000 | Nichols |
| 6,071,280 A | 6/2000 | Edwards et al. |
| 6,090,105 A | 7/2000 | Zepeda et al. |
| 6,107,699 A | 8/2000 | Swanson |
| 6,123,702 A | 9/2000 | Swanson et al. |
| 6,149,647 A | 11/2000 | Tu et al. |
| 6,248,110 B1 | 6/2001 | Reiley et al. |
| 6,251,107 B1 | 6/2001 | Schaer |
| 6,277,112 B1 | 8/2001 | Underwood et al. |
| 6,312,394 B1 | 11/2001 | Fleming, III |
| 6,330,478 B1 * | 12/2001 | Lee et al. ...................... 607/101 |
| 6,358,246 B1 | 3/2002 | Behl et al. |
| 6,369,465 B1 | 4/2002 | Swanson |
| 6,394,949 B1 | 5/2002 | Crowley et al. |
| 6,471,698 B1 | 10/2002 | Edwards et al. |
| 6,554,827 B2 | 4/2003 | Chandrasekaran et al. |
| 6,611,699 B2 | 8/2003 | Messing |
| 6,632,223 B1 | 10/2003 | Keane |
| 6,652,519 B2 * | 11/2003 | Maltese ........................ 606/41 |
| 6,652,520 B2 | 11/2003 | Moorman et al. |
| 6,911,019 B2 | 6/2005 | Mulier et al. |
| 6,949,096 B2 | 9/2005 | Davison et al. |
| 6,960,208 B2 | 11/2005 | Bourne et al. |
| 7,070,595 B2 | 7/2006 | Ormsby et al. |
| 7,108,696 B2 | 9/2006 | Daniel et al. |
| 7,122,033 B2 | 10/2006 | Wood |
| 7,150,747 B1 | 12/2006 | McDonald et al. |
| 7,270,659 B2 | 9/2007 | Ricart et al. |
| 7,666,227 B2 | 2/2010 | Schaller |
| 7,670,374 B2 | 3/2010 | Schaller |
| 7,670,375 B2 | 3/2010 | Schaller |
| 7,717,115 B2 | 5/2010 | Barrett et al. |
| 7,799,024 B2 | 9/2010 | Randall |
| 7,918,795 B2 | 4/2011 | Grossman |
| 7,955,391 B2 | 6/2011 | Schaller |
| 7,963,993 B2 | 6/2011 | Schaller |
| 7,967,865 B2 | 6/2011 | Schaller |
| 8,073,551 B2 | 12/2011 | McCann et al. |
| 8,317,785 B2 | 11/2012 | Faure |
| 9,162,036 B2 | 10/2015 | Caples et al. |
| 2001/0031906 A1 | 10/2001 | Ishikawa et al. |
| 2002/0058937 A1 | 5/2002 | Maltese |
| 2002/0133148 A1 | 9/2002 | Daniel et al. |
| 2002/0151885 A1 | 10/2002 | Underwood et al. |
| 2002/0151886 A1 | 10/2002 | Wood |
| 2003/0065371 A1 | 4/2003 | Satake |
| 2003/0233091 A1 | 12/2003 | Whayne et al. |
| 2004/0024410 A1 | 2/2004 | Olson, Jr. et al. |
| 2004/0054272 A1 | 3/2004 | Messing |
| 2004/0059328 A1 | 3/2004 | Daniel et al. |
| 2004/0064136 A1 | 4/2004 | Papineau et al. |
| 2004/0068157 A1 | 4/2004 | Gellman et al. |
| 2004/0068308 A1 | 4/2004 | Gellman et al. |
| 2004/0082947 A1 | 4/2004 | Oral et al. |
| 2004/0106917 A1 | 6/2004 | Ormsby et al. |
| 2004/0147917 A1 | 7/2004 | Mueller, Jr. et al. |
| 2004/0153120 A1 | 8/2004 | Seifert et al. |
| 2004/0215310 A1 | 10/2004 | Amirana |
| 2004/0254572 A1 | 12/2004 | McIntyre et al. |
| 2005/0004634 A1 | 1/2005 | Ricart et al. |
| 2005/0038419 A9 | 2/2005 | Arnold et al. |
| 2005/0065504 A1 | 3/2005 | Melsky et al. |
| 2005/0070887 A1 | 3/2005 | Taimisto et al. |
| 2005/0085807 A1 | 4/2005 | Venturelli |
| 2005/0125002 A1 | 6/2005 | Baran et al. |
| 2005/0171504 A1 | 8/2005 | Miller |
| 2005/0192654 A1 | 9/2005 | Chanduszko et al. |
| 2005/0205566 A1 | 9/2005 | Kassayan |
| 2005/0216019 A1 | 9/2005 | Eckman |
| 2005/0222557 A1 | 10/2005 | Baxter et al. |
| 2005/0222558 A1 | 10/2005 | Baxter et al. |
| 2005/0234436 A1 | 10/2005 | Baxter et al. |
| 2005/0240176 A1 | 10/2005 | Oral et al. |
| 2005/0251031 A1 | 11/2005 | Smith |
| 2005/0251132 A1 | 11/2005 | Oral et al. |
| 2005/0273091 A1 | 12/2005 | Booth et al. |
| 2006/0095059 A1 | 5/2006 | Bleich et al. |
| 2006/0200121 A1* | 9/2006 | Mowery ............ A61B 18/1477 606/41 |
| 2006/0212056 A1* | 9/2006 | Salvadori et al. ............. 606/167 |
| 2006/0241648 A1 | 10/2006 | Bleich et al. |
| 2006/0241748 A1 | 10/2006 | Lee et al. |
| 2007/0021745 A1 | 1/2007 | McIntyre et al. |
| 2007/0055271 A1 | 3/2007 | Schaller |
| 2007/0055272 A1 | 3/2007 | Schaller |
| 2007/0156130 A1 | 7/2007 | Thistle |
| 2007/0185484 A1 | 8/2007 | Randall |
| 2007/0270924 A1 | 11/2007 | McCann et al. |
| 2007/0282323 A1 | 12/2007 | Woloszko et al. |
| 2008/0004621 A1 | 1/2008 | Dahla et al. |
| 2008/0234680 A1* | 9/2008 | Zaiser et al. .................... 606/71 |
| 2009/0099638 A1 | 4/2009 | Grewe |
| 2010/0057074 A1 | 3/2010 | Roman et al. |
| 2010/0211076 A1 | 8/2010 | Germain et al. |
| 2010/0256619 A1 | 10/2010 | Teitelbaum et al. |
| 2011/0022042 A1 | 1/2011 | Randall |
| 2011/0087255 A1* | 4/2011 | McCormack ...... A61B 5/04005 606/167 |
| 2011/0098708 A9 | 4/2011 | Saadat et al. |
| 2011/0137347 A1 | 6/2011 | Hunziker |
| 2012/0265186 A1 | 10/2012 | Burger |
| 2014/0031715 A1 | 1/2014 | Sherar et al. |
| 2014/0296845 A1 | 10/2014 | Miller et al. |

FOREIGN PATENT DOCUMENTS

| | | |
|---|---|---|
| EP | 0632735 B1 | 10/2001 |
| EP | 1205213 A2 | 5/2002 |
| EP | 1341461 | 6/2002 |
| EP | 1341461 A1 | 9/2003 |
| EP | 1205213 B1 | 10/2005 |
| EP | 1363700 | 11/2005 |
| EP | 1496990 B1 | 12/2010 |
| JP | 4064368 B2 | 3/2008 |

(56) References Cited

FOREIGN PATENT DOCUMENTS

| WO | 1993017756 A1 | 9/1993 |
| WO | 1996/004860 A1 | 2/1996 |
| WO | 1996004860 A1 | 2/1996 |
| WO | 1996/029946 | 10/1996 |
| WO | 1996029946 A1 | 10/1996 |
| WO | 1996039966 A1 | 12/1996 |
| WO | 1999066851 A1 | 12/1999 |
| WO | 2000015130 A2 | 3/2000 |
| WO | 2001013812 A1 | 3/2001 |
| WO | 02054941 A3 | 7/2002 |
| WO | 2004037072 A2 | 5/2004 |
| WO | 2004064606 A2 | 8/2004 |
| WO | 2004/100812 A1 | 11/2004 |
| WO | 2004110258 A2 | 12/2004 |
| WO | 2005122938 A1 | 12/2005 |
| WO | 2005122939 A1 | 12/2005 |
| WO | 2006091597 A1 | 8/2006 |
| WO | 2007112578 A1 | 10/2007 |
| WO | 2010135602 A1 | 11/2010 |
| WO | 2012100355 A1 | 8/2012 |

OTHER PUBLICATIONS

Beaugrand M, N'Kontchou G, Seror O, Ganne N and Trinchet JC, Local/Regional and systemic treatments of hepatocellular carcinoma. Seminars of Liver Disease. 2005. 25, 201-211.
Brezovich IA, Young JH and Wang MT, Temperature distributions in hyperthermia by electromagnetic induction: A theoretical models for the thorax. Medical Physics. 1983. 10 57-65.
Burdio F, Guemes A, Burdio JM, Navarro A, Sousa R. et al, Large Hepatic Ablation with Bipolar Saline-Enhanced Radiofrequency: An Experimental Study in in Vivo Porcine Liver with a Novel Approach. Journal of Surgical Research. 2003 vol. 110 pp. 193-201.
Chiba T, Tokuuye K, Matsuzaki Y, Sugahara S, Chuganji Y, Kagei K, Shoda J, Hata M, Abei M, Igaki H, Tanaka N and Akine Y, Proton Beam Therapy for Hepatocellular Carcinoma: A retrospective review of 162 patients. Clinical Cancer Research, 2005. 11, 3799-3805.
Chin L and Sherar M, Changes in dielectric properties of ex-vivo bovine liver at 915 MHz during heating, Physics in Medicine and Biology. 2001. 46 197-211.
Chute FS and Vermeulen FE, A Visual Demonstration of the Electric Field of a Coil Carrying a Time-Varying Current. IEEE Transactions on Education. 1981. E-24 278-283.
Crowley JD, Shelton J, Iverson AJ, Burton MP, Dalrymple NC and Bishoff JT, Laparoscopic and computed-tomography-guided percutaneous radiofrequency ablation of renal tissue: acute and chronic effects in an animal model. Urology. 2001. vol. 57 pp. 976-980.
Duerig TW, Melton KN, Stöckel D, Wayman CM, Engineering Aspects of Shape Memory Alloys. Butterworth-Heinemann Ltd., Toronto, © 1990, 1-35, 115-136, 193-206, 256-266, 394-413.
Elkamchouchi HM and Salem AL, Helical Antennas with nonuniform diameter. Eighteenth National Radio Science Conference. Mar. 2001. 143-152.
Guerquin-Kern JL, Hagmann MJ, Levin RL, Experimental Characterization of Helical Coils as Hyperthermia Applicators. IEEE Transactions on Biomedical Engineering. 1988. BME-35 46-52.
Iskander M F and Tumeh A M, Design optimization of interstitial antennas. IEEE Transactions on Biomedical Engineering, 1989. 36 238-246.
Jemal A, Murray T, Ward E, Samuels A, Tiwari RC, Ghafoor A, Feuer EJ and Thun MJ, Cancer Statistics 2005, CA Cancer J Clin, 2005. 55 10-30.
Jordan EC and Balmain KG, Electromagnetic Waves and Radiating Systems 2nd Ed. Prentice-Hall, Inc. © 1968, NJ. 100-110, 126-130, 136-139.
Knoepfel H, Magnetic fields: a comprehensive theoretical treatise for practical use. Wiley © 2000, Toronto. 91-125, 201, 202.
Kong FM, Ten Haken RK, Schipper MJ, Sullivan MA, Chen M, Lopez C, Kalemkerian GP and Hayman JA, High-dose radiation improved local tumor control and overall survival in patients with inoperable/unresectable non-small-cell lung cancer: Long-term results of a radiation dose escalation study, Int. J. Radiation Oncology Biol. Phys. 2005. 63 No. 2 324-333.
Kumaradas JC and Sherar MD, An edge-element based finite element model of microwave heating in hyperthermia: method and verification. International Journal of Hyperthermia. 2002. 18 426-440.
Lagerwaard FJ, Senan S, Van Meerbeck JP, Graveland WJ, Has 3-D conformal radiotherapy (3D CRT) improved the local tumor control for stage I non-small cell lung cancer? Radiotherapy & Oncology. 2002. 63 151-157.
Lorrain P and Corson D, Electromagnetic Fields and Waves. W. H. Freeman and Company, © 1962, New York. 276-286, 298-299, 308-319, 332-339, 342-351, 422-425.
McGahan JP and Dodd GD, Radiofrequency Ablation of the Liver: Current Status. AJR. 2001. 176 3-16.
McLoud TC, Lung Cancer: Imaging techniques for diagnosis and staging of lung cancer, Clinics in Chest Medicine, 2002. 23 No. 1 123-136.
McDonald, M, Lochhead S, Chopra R and Bronskill MJ, Multi-modality tissue-mimicking phantom for thermal therapy. Physics in Medicine and Biology. 2004. 49 2767-2778.
Moore LE, Wilson RT and Campleman SL, Lifestyle factors, exposures, genetic susceptibility, and renal cell cancer risk: a review. Cancer Invest 2005. 23 240-255.
Mountain CF, Revisions in the international system for staging lung cancer. Chest, 1997. 11 1710-1717.
Namjoshi KV and Biringer PP, Multiple conductor induction problem: Analytical approach. American Institute of Physics. 1990. 67 4732-4734.
Namjoshi KV and Biringer PP, Multiple conductors in transverse magnetic field and their application in magnetic shielding. IEEE Transactions on Magnetics. 1991. 27 3916-3919.
Rendon RA, Gertner MR, Sherar MD, Asch MR, Kachura JR, Sweet J and Jewett Mas, Development of a radiofrequency based thermal therapy technique in an in-vivo porcine model for the treatment of small renal masses. The Journal of Urology. 2001. 166 292-298.
Ryan TP, Mechling JA and Strohbehn JW, Absorbed power deposition for various insertion depths for 915 MHz interstitial dipole antenna arrays: experiment versus theory. Int J Radiation Oncology Biol. Phys. 1990. 19 377-387.
Ryff PF, Current Distribution in Helical Solenoids, IEEE Transactions on Industry Applications. 1972. 8 485-490.
Stöckel D, Nitinol Medical Devices and Implants. SMST-2000 Conference Proceedings, 2001, 531-541.
Stuchly MA and Stuchly SS, Coaxial Line Reflection methods for Measuring Dielectric Properties of Biological Substances at Radio and Microwave Frequencies—A review. IEEE Trans. Instrum. Meas. 1980. 176-183.
Stuchly MA and Stuchly SS, Measurement of Radio Frequency Permittivity of Biological Tissues with an Open-Ended Coaxial Line : Part I. IEEE Transactions on Microwave Theory and Techniques. 1982. 30 82-86.
Stuchly MA and Stuchly SS, Dielectric Properties of Biological Substances—Tabulated. Journal of Microwave Power. 1980.15 20-25.
Tamaki K, Shimizu I, Oshio A, Fukano H, Lnoue H et al. Influence of large intrahepatic blood vessles on the gross and histological characteristics of lesions produced by radiofrequency ablation in a pig liver model. Liver International. 2004. vol. 24 pp. 696-701.
Wright AS, Sampson LA, Warner TF, Mahvi DM, Lee FT, Radiofrequency versus Microwave Ablation in a Hepatic Porcine Model. Radiology. 2005. vol. 236 pp. 132-139.
Varkarakis IM, Allaf ME, Lnagaki T, Bhayani SB, Chan DY, Su LM, Jarrett TW, Kavoussi LR and Soloman SB, Percutaneous radio frequency ablation of renal masses: results at a 2 year mean follow-up. The Journal of Urology, 2005. 174 456-460.

(56) References Cited

OTHER PUBLICATIONS

NDC Nitinol Devices & Components, Nitinol SE508 Wire Material Data Sheet, California NDC: Feb. 2002 (http://www.nitinol.info/pdf_files/se508_wire_data.pdf).
International Preliminary Report on Patentability dated Oct. 8, 2008 in respect of International Application No. PCT/CA2007/000547.
International Preliminary Report on Patentability dated Jul. 30, 2013 in respect of International Application No. PCT/CA2012/050053.
Lui, K.W. et al., Radiofrequency ablation of renal cell carcinoma. Clinical Radiology, 58: 905, 2003.
Aron, M. et al., Renal tumor ablation. Current Opinion in Urology, 15: 298, 2005.
Ahrar, K. et al., Percutaneous radiofrequency ablation: minimally invasive therapy for renal tumors. Expert Review of Anticancer Therapy, 6: 1735, 2006.
Jemal A. et al. Annual Report to the nation on the status of cancer, 1975-2005, featuring trends in lung cancer, tobacco use, and tobacco control. J Natl Cancer Inst 100 (23): 1672-1694, 2008.
Georgy BA. Metastatic Spinal lesions: State-of-the-Art treatment Options and Future Trends. AJNR. 29:1605-1611, 2008.
Sundaresan N. et al. Surgery for solitary metastases of the spine: rationale and results of treatment. Spine. 27: 1802-1806, 2002.
Bilsky MH. et al. Intralesional resection of primary and metastatic sarcoma involving the spine: outcome analysis of 59 patients. Neurosurgery 49: 1277-1286, 2001.
Kassamali RH. et al. Pain management in spinal metastases: the role of percutaneous vertebral augmentation. Annals of Oncology. Review. 2010.
Davidson Sr. et al. Treatment planning and dose analysis for interstitial photodynamic therapy of prostate cancer. Phys Med Biol, 54: P2293, 2009.
Bayer E et al. "Sphenopalatine ganglion pulsed radiofrequency treatment in 30 patients suffering from chronic face and head pain", Journal of Pain Practice, 5: 223-7, 2005.
Prummer R. et al. "NITINOL ®—Stainless steel compound materials, made by explosive welding", Fundamental Issues and Applications of Shock-Wave and High-Strina-Rate Phenomena, Proceedings, 581-4, 2001.
Adachi A. et al. "Heat distribution in the spinal canal during radiofrequency ablation for vertebral lesions: Study in swine", Radiology 247(2), 374-80, 2008.
Kurup et al., Ablation of Skeletal Metastases: Current Status, J Vasc Interv Radiol, 2010, 21, p. S242-S250.
Edgar, M.A. et al., The nerve supply of the lumbar intervertebral disc, The Journal of Bone & Joint Surgery, vol. 89-8, No. 9, Sep. 2007.
Benvenue Medical, Inc., Advancing Spine Repair, pages from website, http://benvenuemedical.com/company/about, printed Jul. 23, 2011.
Non-Final Office Action. U.S. Appl. No. 13/954,647, dated Jan. 13, 2015.
Final Office Action. U.S. Appl. No. 13/954,647, dated Jul. 24, 2015.
Final U.S. Office Action in relation to corresponding U.S. Appl. No. 13/954,647, dated Sep. 28, 2016.
Office Action Response in relation to corresponding U.S. Appl. No. 13/954,647, dated Apr. 13, 2015.
Office Action Response in relation to corresponding U.S. Appl. No. 13/954,647, dated Dec. 24, 2015.
Office Action in relation to corresponding U.S. Appl. No. 13/954,647, dated Mar. 9, 2016.
Applicant summary of interview with Examiner in relation to corresponding U.S. Appl. No. 13/954,647, dated Jun. 7, 2016.
Office Action Response in relation to corresponding U.S. Appl. No. 13/954,647, dated Jun. 9, 2016.
Applicant Initiated Interview Summary in relation to corresponding U.S. Appl. No. 13/954,647, dated Jun. 10, 2016.
Response to Office Action dated Nov. 28, 2016 in related U.S. Appl. No. 13/954,647.
Final Office Action dated Feb. 28, 2017 in related U.S. Appl. No. 13/954,647.
Response to final Office Action dated May 29, 2017 in related U.S. Appl. No. 13/954,647.
Advisory Action dated Jun. 23, 2017 in related U.S. Appl. No. 13/954,647.
Non-final Office Action dated Dec. 27, 2017 in related U.S. Appl. No. 13/954,647.

* cited by examiner

COIL ELECTRODE FOR THERMAL THERAPY

CROSS REFERENCE TO RELATED APPLICATIONS

This is a national stage application of International Application No. PCT/CA2012/050053 filed Jan. 30, 2012, which claims priority to U.S. Provisional Application No. 61/437,653 filed Jan. 30, 2011, and the entire contents of each are hereby incorporated herein by reference.

FIELD

Various embodiments are described herein that relate to a coil electrode that can be used to heat tissue.

BACKGROUND

U.S. Publication No. 20070270924 and International Publication No. WO2007/112578 describe a single-coil RF (radio frequency) electrode, along with an associated method of operation, for use in an RF applicator, RFA (radio frequency ablation) apparatus or RFA system for heating tumors, including large tumors with a single heating session. The RF electrode generally has a helical geometry, although many variations exist, and is provided with an excitation current having a frequency that is sufficient for magnetic induction and coupling of various electric and magnetic fields to produce an electric field within the volume surrounded by the coil for directly applying heat to the tissue therein. U.S. Publication No. 20070270924 and International Publication No. WO/2007/112578 are each hereby incorporated herein by reference in their entirety.

DETAILED DESCRIPTION

Figure 1:
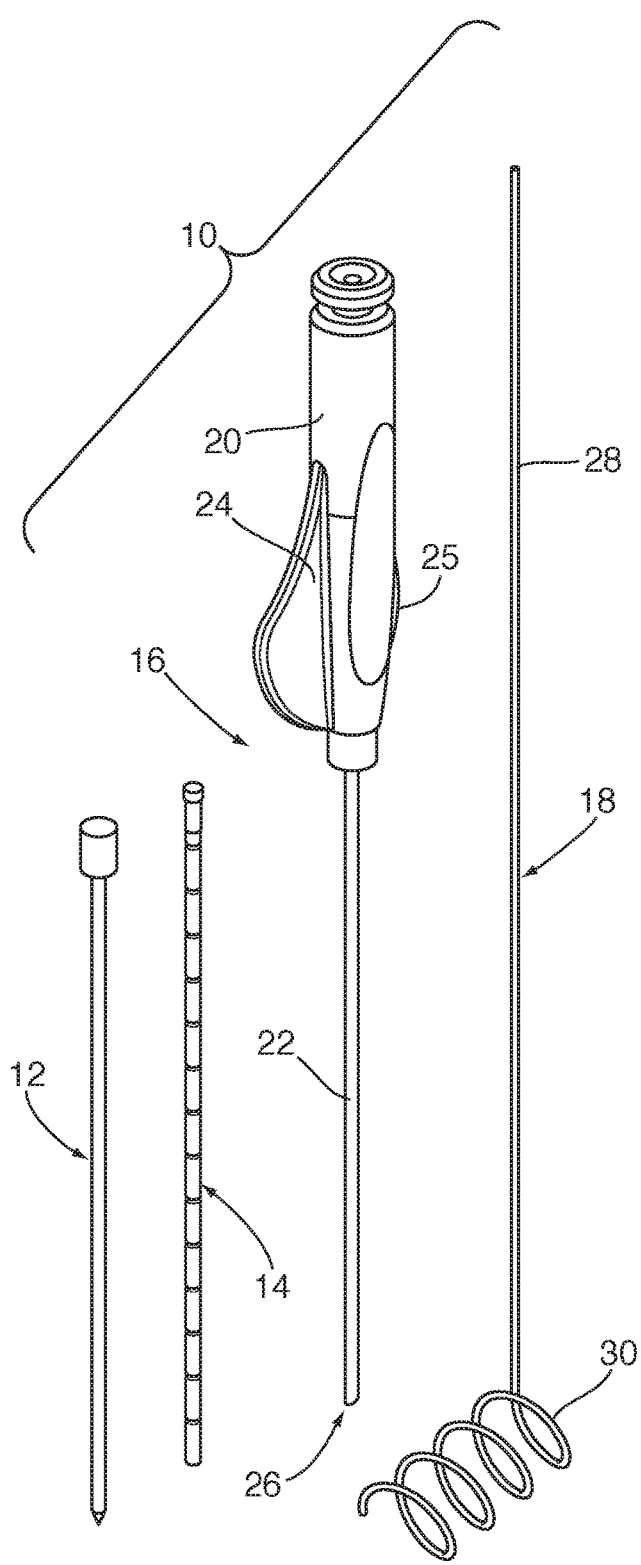
FIG. 1 shows an example of an RFA apparatus.

It will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

Figure 2:
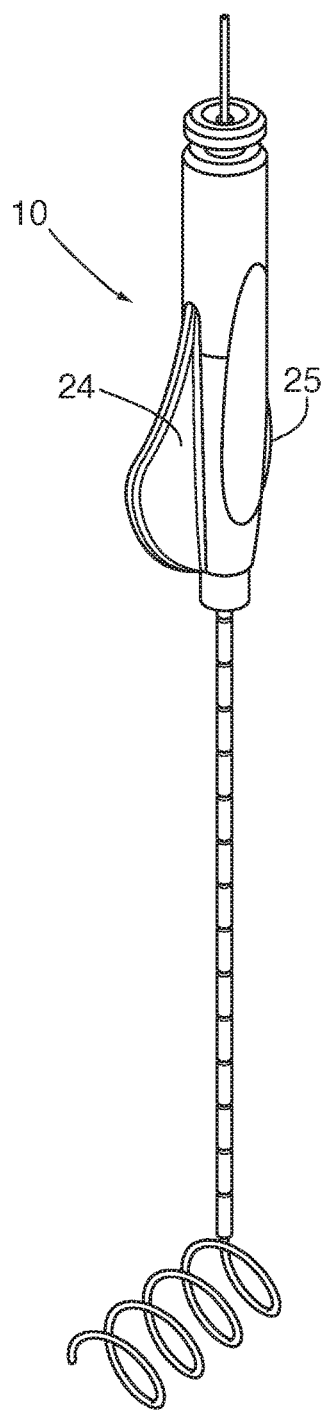
FIG. 2 shows the RFA apparatus of FIG. 1 in an assembled state.

Referring to FIG. 1, an example of an RFA (radio frequency ablation) apparatus is shown generally at 10. The RFA apparatus 10 comprises a trocar 12, an introducer sheath 14, an applicator 16 and a coil electrode 18. The applicator 16 comprises a handle 20 and a cannulating delivery needle 22 mounted to the handle 20. The handle 20 comprises a radially-projecting fin 24. The cannulating delivery needle 22 comprises a tip 26 spaced apart from the handle 20. The introducer sheath 14 can be sized and shaped to slidingly receive the cannulating delivery needle 22, and can be couplable to the handle 20 using a luer lock mechanism. The trocar 12 can be sized and shaped to be slidingly received within the introducer sheath 14. The coil electrode 18 comprises a lead portion 28 and helical portion 30 coupled to the lead portion 28. The RFA apparatus 10 assembled (not including the trocar 12) can be seen in FIG. 2.

In use, the helical portion 30 of the coil electrode 18 has a retracted state when housed within the cannulating delivery needle 22 and a deployed state when moved out of the tip 26 of the cannulating delivery needle 22. At least the helical portion 30 of the coil electrode 18 can be constructed from a shape memory, electrically conductive alloy to allow for the percutaneous deployment of the coil electrode into a tumor tissue in a minimally invasive fashion. In various examples, the helical portion 30 of the coil electrode 18 can be formed of Nitinol. Nitinol has an electrical conductivity similar to that of stainless steel, is MR compatible, biocompatible, and has very high corrosion resistance. However, it has been observed that superelastic metals such as Nitinol exhibit an aged stress-strain curve that is time dependent. For this reason, the helical portion 30 of the coil electrode 18 should not be left in the retracted state, housed within the cannulating delivery needle 22, until right before deployment (for example, within 20 to 30 minutes).

Figure 3:
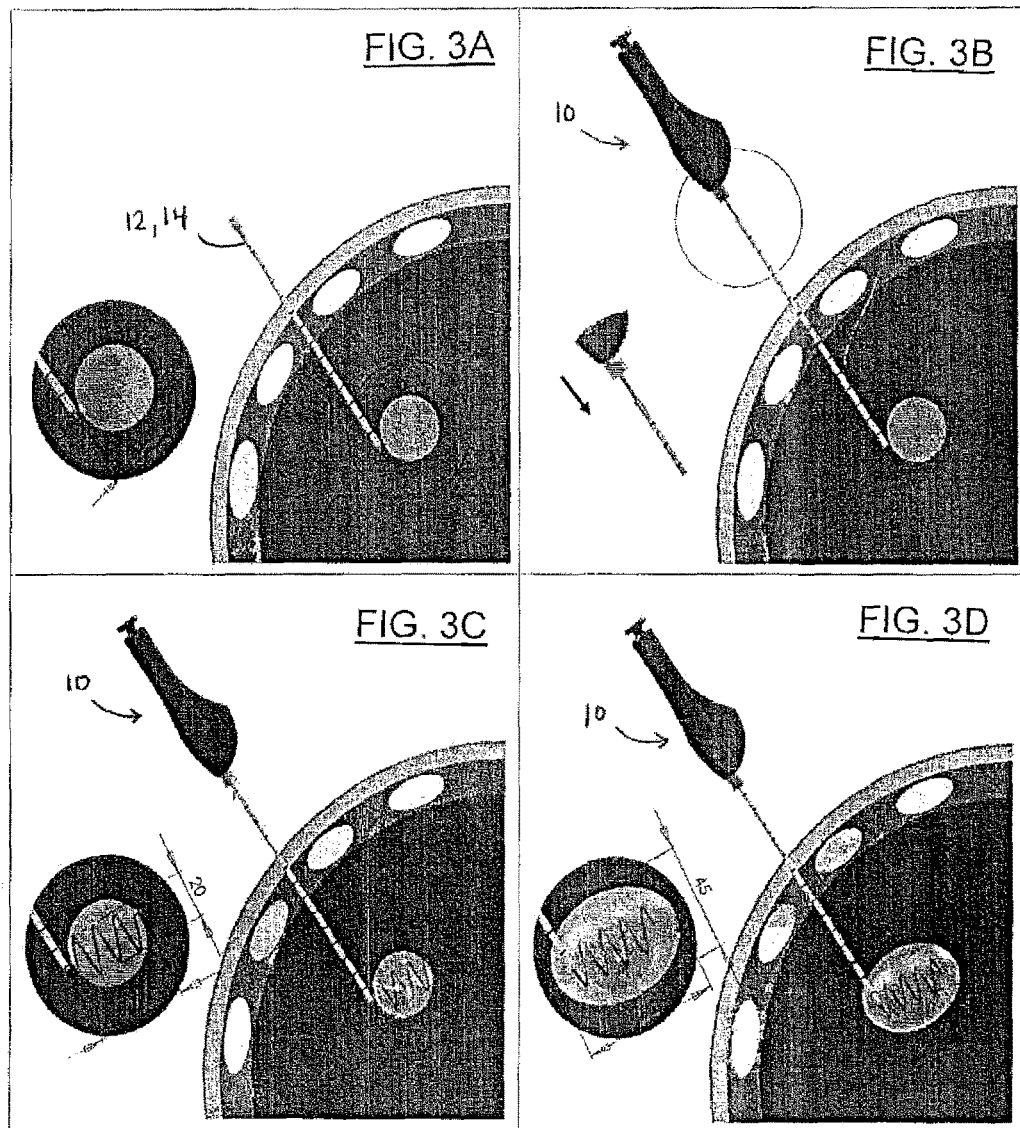
FIGS. 3A to 3D illustrate use of the RFA apparatus of FIG. 1.

General instructions for use of the RFA apparatus 10 can be seen in FIGS. 3A to 3D. Referring to FIG. 3A, the introducer sheath 14 and the trocar 12, received within the introducer sheath 14, can be inserted into the tissue, and the tip of the introducer sheath can be positioned, for example, about 2 cm away from the center of the tumor. Referring to FIG. 3B, the trocar 12 can be removed from the introducer sheath 14, the helical portion 30 of the coil electrode 18 can be retracted within the cannulating delivery needle 22, and the cannulating delivery needle 22 can be inserted into the introducer sheath 14. The introducer sheath 14 can be locked to the handle 20 using a luer lock mechanism, for example. Referring to FIG. 3C, the helical portion 30 can be deployed out of the tip 26 of the cannulating delivery needle 22 and into the tumor. Referring to FIG. 3D, the tumor can be ablated.

In some particular examples, the helical portion 30 of the coil electrode 18 may be fabricated of Nitinol SE510 (NDC-Nitinol Devices & Components, Fremont, Calif.) or a similar material with generally equivalent mechanical properties.

This material results in a coil electrode that, when deployed at high speeds (for example, deployment of 3 to 4 cm long helical portion 30 within 4 to 5 seconds), exhibits a decrease in final coil expansion, as compared to SE508, for example.

Figure 4:
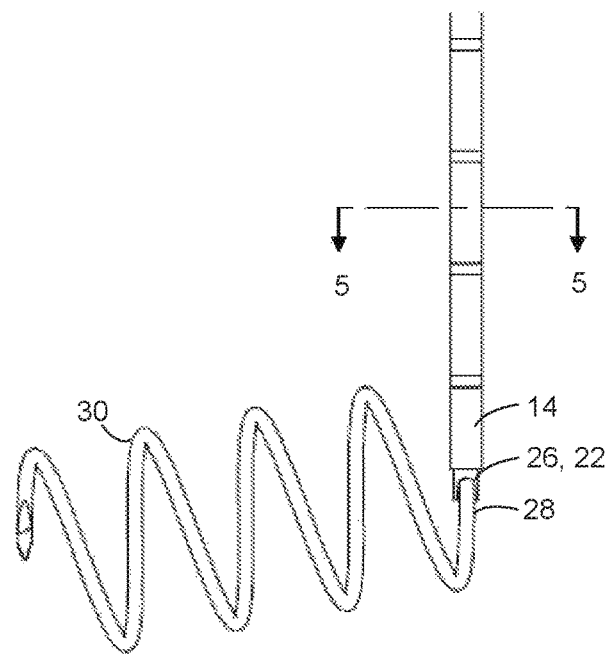
FIG. 4 shows a detailed view of a helical portion of a coil electrode and a tip of a cannulating delivery needle of the RFA apparatus of FIG. 1.
Figure 5:
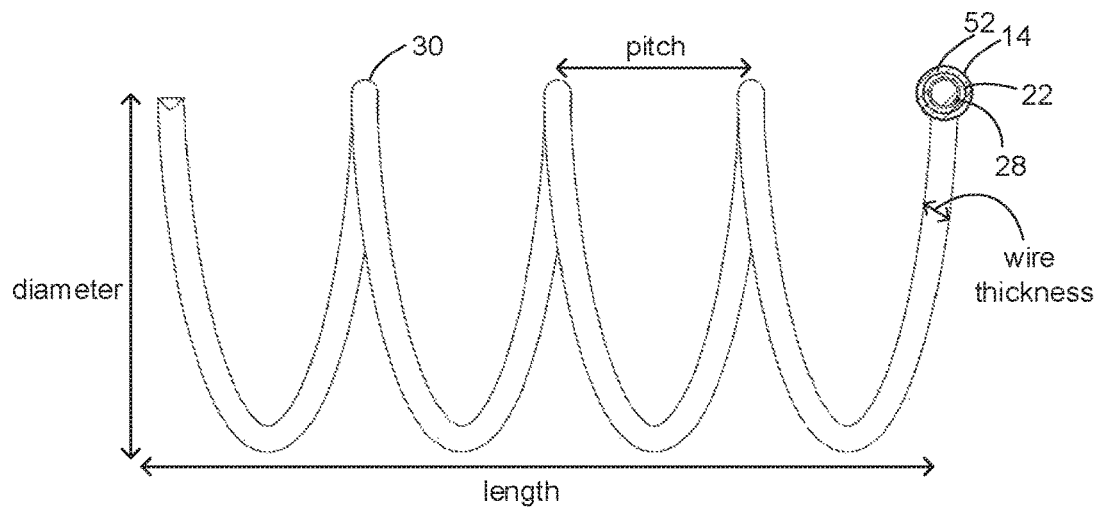
FIG. 5 is a sectional view along line 5-5 of FIG. 4.

In some particular examples, and referring to FIGS. 4 and 5, the helical portion 30 can have a wire thickness of between 1.3 and 1.4 mm, or about 1.345 mm. The helical portion 30 can have a diameter of between 17 and 20 mm, or about 18 mm. The helical portion 30 can have a pitch of between 8 to 12 mm, or about 10 mm. The helical portion 30 can have a length of between 3 to 4 cm.

Figure 6:
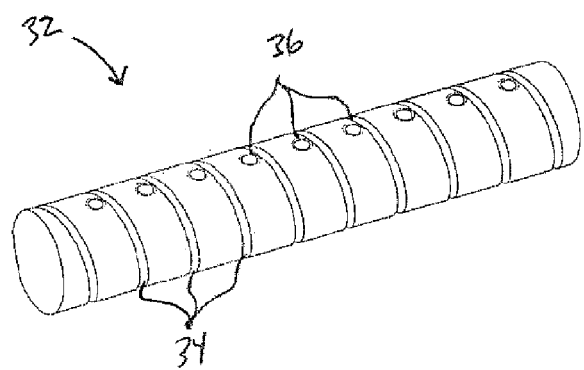
FIG. 6 shows a jig for setting the shape of the helical portion of the coil electrode of FIGS. 4 and 5 during annealing.

Referring to FIG. 6, a generally cylindrical jig 32 can be used to prepare the helical portion 30. The jig 32 comprises helical grooves 34 for retaining the wire, and screw holes 36 can be provided adjacent to the grooves 34, aligned along one side of the jig 32. Screws (not shown) can be fastened to the screw holes 36 to maintain the wire in a set position within the grooves 34 during annealing.

As an example, a straight, 1.345 mm diameter round wire sample of Nitinol can be wound onto a 18 mm diameter cylindrical jig with a 10 mm pitch helical groove, forming a helical coil. To reduce a slight curvature that may be present in the lead portion of the wire extending from the jig, a 12-gauge needle can be slid over the lead portion to straighten the wire before annealing. The wire/jig assembly can be heat-treated in an annealing oven (TLD Annealing Furnace, Radiation Products Design, Inc., Albertville, Minn.) for about 12 minutes at an average temperature of 600° C. After heating, the wire/jig assembly can be rapidly quenched in water at room temperature. This heat treatment procedure is designed to produce a supereleastic coil, whereby mechanical deformation of the coil above its transformation temperature causes stress-induced phase transformation from Austenite to Marstensite. The stress-induced Martensite is unstable at temperatures above the Austenite finishing temperature so that, when the stress is removed, the Nitinol will spring back to the Austenite phase and its pre-stressed shape. Heat treating for longer or shorter than 12 minutes (±20 seconds) can result in a coil when deployed into tissue will exhibit a higher degree of plastic deformation and coil diameter and pitch expansion.

Figure 7:
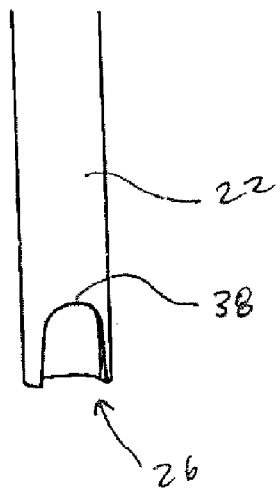
FIG. 7 is a detailed view of the tip of the cannulating delivery needle of FIG. 4.
Figure 8:
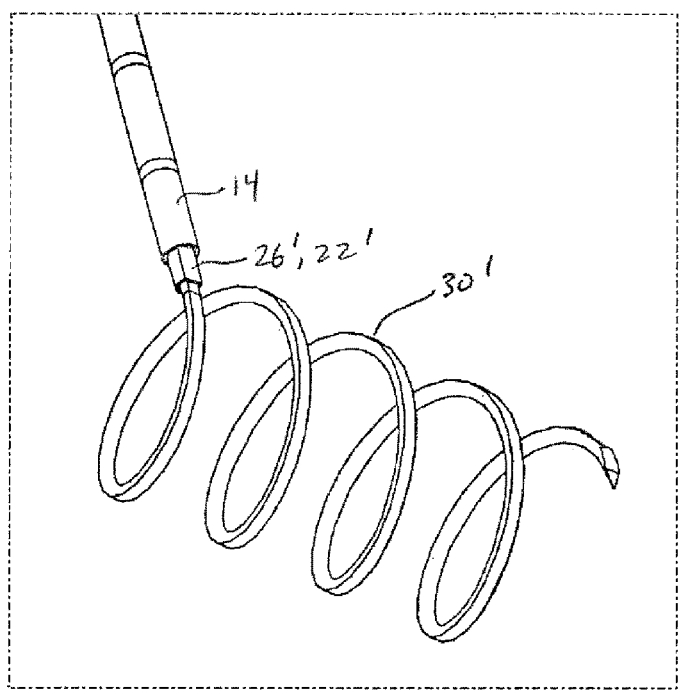
FIG. 8 shows a detailed view of another helical portion of a coil electrode and tip of a cannulating delivery needle.
Figure 9:
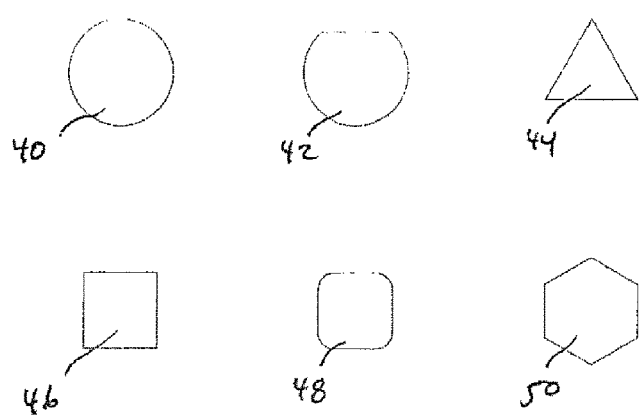
FIG. 9 shows examples of wire cross sectional shapes.

An observed phenomenon of the coil electrode 18 is that it will spin axially relative to the cannulating delivery needle 22 when it is deployed. The spin phenomenon is the result of torsion stress being released as the helical portion 30 of the coil electrode 18 emerges from the tip 26. The spin direction is dependent on the direction in which the wire of the helical portion 30 is oriented relative to the cannulating delivery needle 22. To combat this phenomenon, when deployed, an extra coil of the helical portion 30 may be kept remaining inside the cannulating delivery needle 22 to exert pressure against the walls of the cannulating delivery needle 22, in order to restrict rotation. Furthermore, referring to FIG. 7, the tip 26 of the delivery needle 22 can comprise a slot 38 for guiding deployment of the helical portion 30 in a consistent direction, ensuring that the helical portion is deployed from the tip 26 in a predictable manner. Moreover, the cannulating delivery needle 22 and the wire forming the helical portion 30 can have complementary cross sectional shapes that prevent the helical portion 30 from rotating relative to the cannulating delivery needle 22, enabling predictable deployment. Referring to FIG. 8, a coil portion 30' and a tip 26' of a cannulating delivery needle 22' are shown having complementary cross sections in the shape of a circular segment (circular with a flat side). FIG. 9 illustrates some possible cross sectional shapes for wires for the helical portion of the coil electrode, including a circle 40, a circular segment 42, a triangle 44, a square 46, a squircle 48, and a hexagon 50. FIG. 9 is not exhaustive, as there are various other possible shapes.

The inventors have determined that it is feasible to deploy a 1.345 mm Nitinol SE510 coil, measuring 18 mm in diameter, 40 mm long and with a 10 mm pitch, into liver and kidney tissue, while also producing the necessary uniform electric fields to heat and coagulate a large target volume within a short treatment time of less than 8 minutes.

Figure 10:
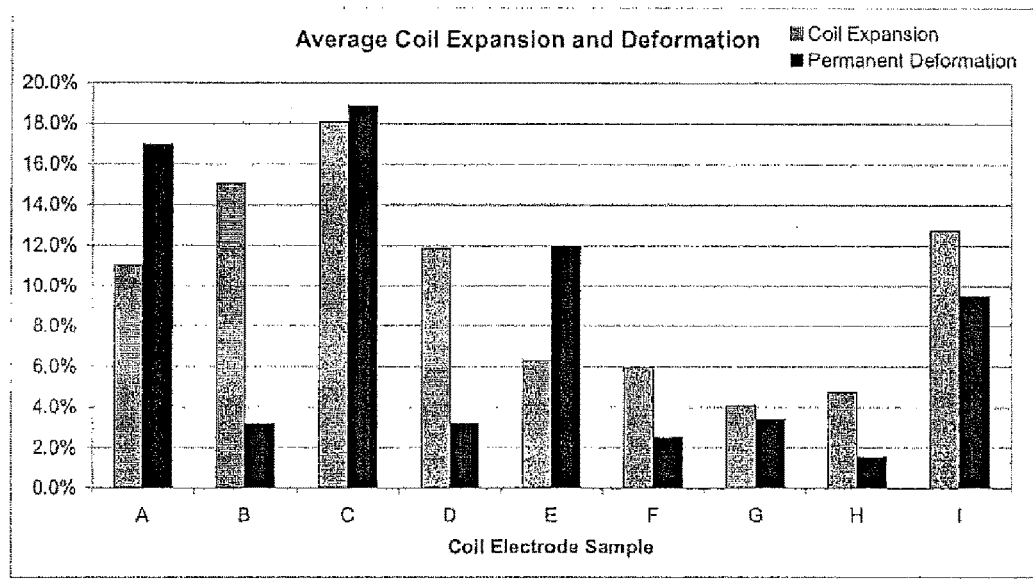
FIG. 10 illustrates average coil expansion and deformation for different coil samples.

Referring to FIG. 10, and with reference to Table 1 below, the coil geometry designated as sample G may produce minimal coil expansion and plastic deformation when deployed. Successful deployment, characterized by maintenance of the helical coil's shape and trajectory, was evaluated with a digital camera by recording the deployment of the helical coil into a translucent tissue mimicking gelatin phantom. Deployment was also validated by computed tomography, using CT scans of the coil electrode deployed into liver and kidney tissue.

TABLE 1

Coil electrode samples.

| Sample | Material | Diameter (mm) | Pitch (mm) | Thickness (mm) |
|---|---|---|---|---|
| A | SE508 | 15 | 10 | 1.4 |
| B | SE508 | 15 | 10 | 1.5 |
| C | SE508 | 18 | 10 | 1.4 |
| D | SE508 | 18 | 10 | 1.5 |
| E | SE510 | 17 | 10 | 1.1 |
| F | SE510 | 18 | 10 | 1.1 |
| G | SE510 | 18 | 10 | 1.34 |
| H | SE510 | 17 | 10 | 1.34 |
| I | SE510 | 19 | 10 | 1.34 |

The frequency range of the excitation current signal to ablate tumors can be, for example, in the range of 5 to 50 MHz, as described U.S. Publication No. 20070270924. An RF coil electrode as per the sample G configuration was tested at 27.12 MHz. The operating frequency was sufficient enough to promote magnetic induction but low enough to minimize the effects of the opposing induction fields set up by the induced eddy currents. This frequency produced an electric field within the volume surrounded by the coil for directly applying heat to the tissue therein.

An RF coil electrode as per the sample G configuration underwent ex vivo and in vivo testing to validate its ability to coagulate large homogenous volumes in liver and kidney tissue. The RF coil electrode was used to treat 16 resected livers. Ex vivo testing was successful with an average ellipsoidal ablation volume of 56.4 (±19.6) cm$^3$ and treatment time of 8.2 (±3.4) minutes. The RF coil electrode was used to treat the livers and kidneys of 8 pigs. Gross inspection showed average ellipsoidal ablation volumes in kidney and liver measuring 33.2 (±17.4) cm$^3$ and 51.5 (±17.2) cm$^3$, for an average treatment time of 10.4 (±4.8) and 10.8 (±5.1) minutes, respectively. Temperatures upwards of 90° C. were measured in the central region of the ablation zone. Histological and enzymatic examination showed uniform cell necrosis with no enzymatic activity within the lesion's boundary and a sharp transition between viable and non-viable tissue.

Referring again to FIG. 1, the handle 20 of the applicator 16 can be generally cylindrical and formed of a plastic material. The fin 24 projects radially from the handle 20 and extends generally parallel to a longitudinal axis of the handle 20. The fin 24 allows the user to hold the apparatus 10 in a comfortable, stylus-like manner. Furthermore, the fin 24 can indicate a deployment path direction of the helical portion 30 of the coil electrode 18. Although a centerline of the fin 24 can be generally aligned with a longitudinal axis of the cannulating delivery needle 22, a longitudinal axis of the helical portion 30 can be offset from the longitudinal axis of the cannulating delivery needle 22. For this reason, a second fin 25 may be used to indicate the center of the ablation zone. Another function of the fin 24 is that it can inform the user of the relative success of the deployment trajectory of the helical portion 30 into tissue. If the helical portion 30 encounters resistance within the tissue during deployment, the fin 24 will be caused to rotate about the handle 30, alerting the user with tactile feedback.

It should be appreciated that, when retracted into the cannulating delivery needle 22, the helical portion 30 may exert a considerable amount of bending force on the cannulating delivery needle 22, causing an undesirable deflection of the tip 26. The cannulating delivery needle 22 may be fabricated out of various materials. However, the inventors have determined that it is the size of the cannulating delivery needle 22 that can substantially reduce the amount of deflection. Bending stress in a beam under simple bending can be analyzed using the Euler-Bernoulli beam equation and Hooke's law, as follows.

$$\sigma = \frac{My}{I_x} = E\varepsilon,$$

where: $\sigma$ is the bending stress; M is the moment about the neutral axis; y is the perpendicular distance to the neutral axis; $I_x$ is the second moment of inertia about the neutral axis x; E is Young's Modulus; and $\varepsilon$ is strain. The inventors have observed that the moment of inertia value can have a more significant impact on the bending stress than the material's Young's Modulus value.

The introducer sheath 14 may also provide rigid support to the cannulating delivery needle 22, thereby reducing the deflection of the tip 26. The introducer sheath 14 may also allow biopsies to be conducted before conducting the RF treatment. The introducer sheath 14 can also function to insulate surrounding tissues from the RF energies.

Figure 11:
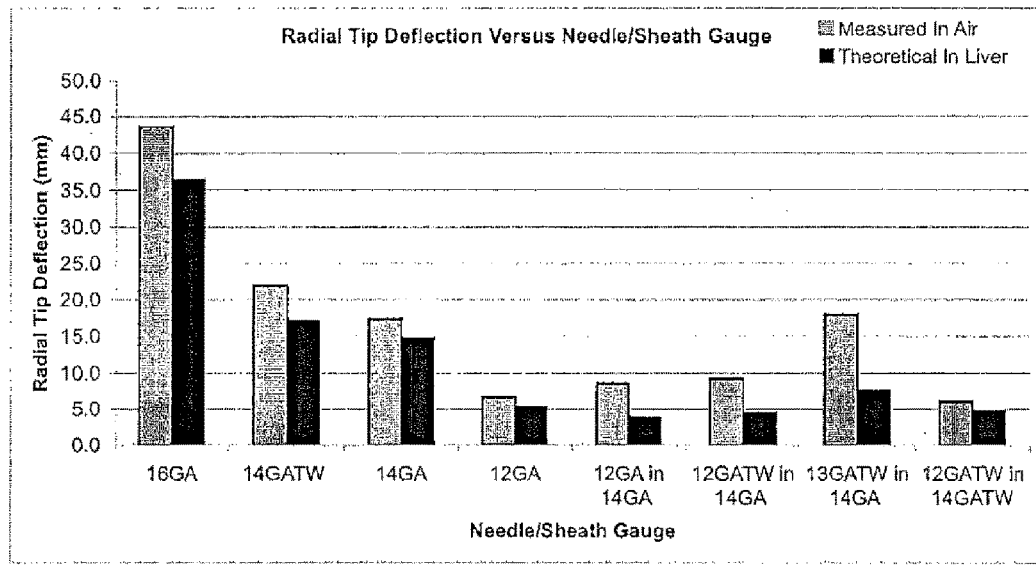
FIG. 11 illustrates radial tip deflection for different needle and sheath configurations.

FIG. 11 shows measured and calculated results for different needle and needle/sheath configurations, indicating that a 14-gauge regular wall surgical grade stainless tube used as the needle and a 12-gauge regular wall surgical grade stainless tube used as the sheath may result in a reduced needle tip deflection. The introducer sheath may also include a layer of an electrically insulating outer cladding material (designated 52 in FIG. 5), for example, clear and flexible ⅛" polyolefin heat-shrink tubing (McMaster-Carr, Cleveland, Ohio).

However, the cannulating delivery needle 22 may be directly inserted into the body without first inserting the introducer sheath 14, in which case the cannulating delivery needle 22 can have a slightly larger diameter needle; a 12-gauge needle would suffice for use with a helical coil 30 having a wire thickness of 1.345 mm.

Figure 12:
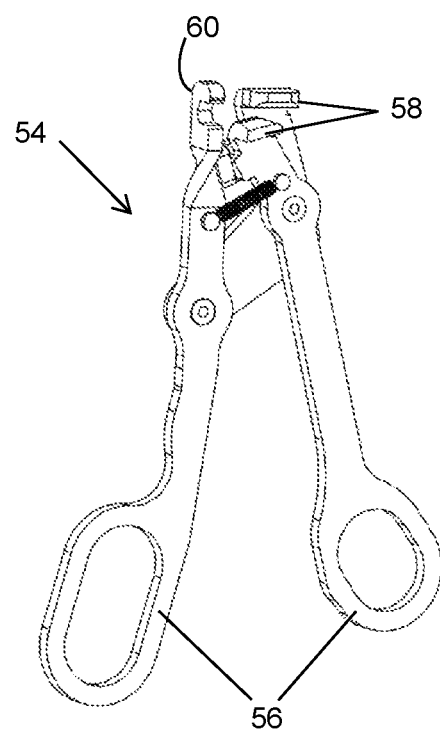
FIG. 12 shows a hand tool.
Figure 13:
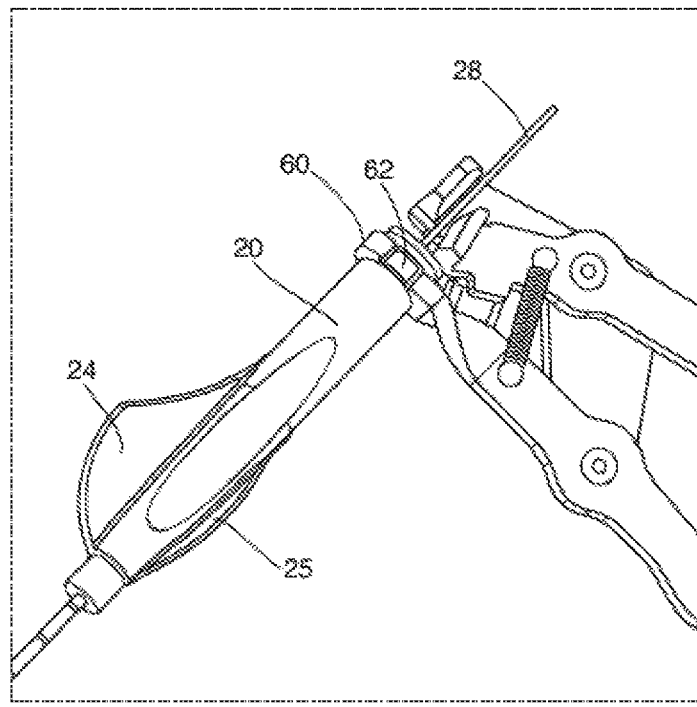
FIG. 13 is a detailed view of the retractor hand tool of FIG. 12 in use with the RFA apparatus of FIG. 1.
Figure 14:
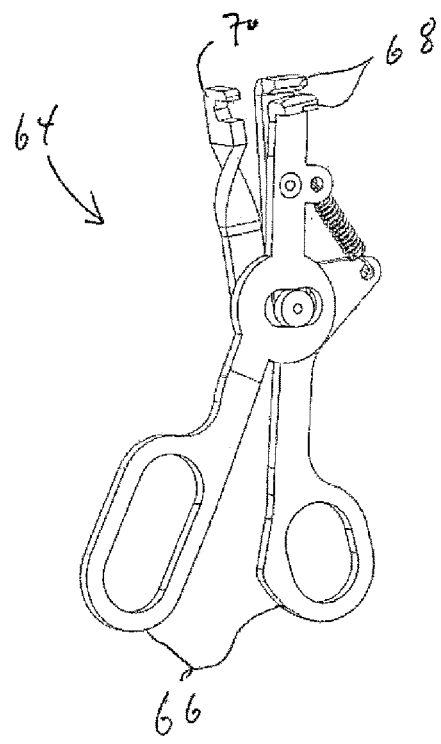
FIG. 14 shows another hand tool.

Referring to FIG. 12, a hand tool 54 is configured for use to retract the helical portion 30 into the cannulating delivery needle 22 (FIG. 1). The hand tool 54 comprises a pair of lever arms 56 that are operable to control a pair of generally opposing clamp jaws 58. Referring to FIGS. 12 and 13, the hand tool 54 further comprises an arm 60 that engages a circumferential recess 62 provided on the handle 20. The recess 62 can have a hexagonal cross sectional shape, and the arm 60 can have a complementary wrench slot that engages the recess 62 and limits rotation of the hand tool 54 about the handle 20. Actuation of the lever arms 56 causes the clamp jaws 58 to grasp the lead portion 28 and move the lead portion 28 away from the handle 20. Referring to FIG. 14, a hand tool 64 is similar to the hand tool 54, but is configured to deploy the helical portion 30 from the tip 26 of the cannulating delivery needle 22 (FIG. 1). Actuation of lever arms 66 causes clamp jaws 68 to grasp the lead portion 28 and move the lead portion 28 towards the handle 20, which is engaged by arm 70.

As described above, the cannulating delivery needle 22 can be inserted into tissue of the patient at the site of the tumour. The user can then deploy the helical portion 30 partially, using the hand tool 64, and the position of the helical portion 30 can be examined using one or more imaging modalities. If the helical portion 30 is correctly placed relative to the tumour, the user may continue to advance the lead portion 28 to deploy the helical portion 30. If the helical portion 30 is not correctly placed, the user may retract the lead portion 28, using the hand tool 54. Manual deployment offers the benefit of tactile feedback and may lessen concerns regarding sterilization, compared with, for example, an assisted device with various components.

Figure 15:
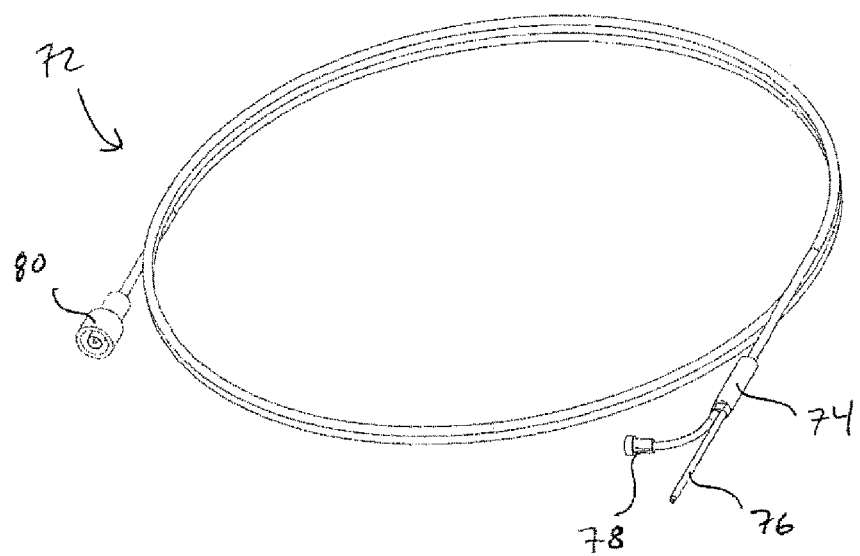
FIG. 15 shows a cable for use with the RFA apparatus of FIG. 1.

Referring to FIG. 15, an RF delivery cable 72 can be a flexible coaxial cable, for example, a 6 foot long RG 58 C/U cable. The cable 72 comprises a breakout connection 74 that is proximal to an applicator connector 76, which is configured to electrically connect to the lead portion 28 extending from the applicator 16 (FIG. 1). The cable 72 can comprise an outer metal shield (not shown) that terminates at the breakout connection 74 at a grounding electrode connector 78. The grounding electrode (not shown) may consist of two or more dispersive electrodes. At the other end, the cable 72 terminates at a connector 80. The breakout connection 74 near the applicator connector 76 can limit RF loss along the cable 72. Preferably, there is no metal shielding between the grounding electrode connector 78 and the applicator connector 76, otherwise there may be capacitive coupling which may result in increased impedance and heating of the coaxial cable.

It should be understood that various modifications can be made to the embodiments described and illustrated herein, without departing from the invention, the scope of which is defined in the appended claims.

We claim:

1. An RFA (radio frequency ablation) apparatus, comprising:
    an applicator, the applicator including a handle and a cannulating delivery needle mounted to the handle, the cannulating delivery needle including a tip spaced apart from the handle;
    a coil electrode, the coil electrode including a lead portion housed in the cannulating delivery needle, and a helical portion coupled to the lead portion, the helical portion formed of Nitinol and having a retracted state when housed within the cannulating delivery needle and a deployed state when moved out of the tip of the cannulating delivery needle, the helical portion having a central axis that is offset from the longitudinal axis of the cannulating delivery needle;
    a radially projecting first fin on the handle, the first fin being positioned to indicate a deployment path direction of the helical portion of the coil electrode, the first fin extends along half of the handle adjacent to the cannulating delivery needle and the first fin is caused to rotate about the handle to alert a user of the apparatus with tactile feedback when the helical portion encounters resistance when deployed; and a second fin being aligned with the central axis of the helical portion of the coil electrode when it is in its deployed position to indicate a center of an ablation zone during use.

2. The apparatus of claim 1, wherein the helical portion is formed of Nitinol SE510, has a wire thickness between 1.3 and 1.4 mm, has a pitch between 8 to 12 mm and a length between 3 to 4 cm.

3. The coil electrode of claim 2, wherein the helical portion has a wire thickness of about 1.345 mm.

4. The coil electrode of claim 3, wherein the helical portion has a diameter of between 17 and 20 mm.

5. The coil electrode of claim 4, wherein the helical portion has a diameter of about 18 mm.

6. The coil electrode of claim 2, wherein the helical portion has a pitch of about 10 mm.

7. The coil electrode of claim 2, wherein the helical portion generally has a wire cross sectional shape selected from a circular segment, a triangle, a polygon, and a squircle.

8. The apparatus of claim 1, wherein the handle is generally cylindrical.

9. The apparatus of claim 1, wherein the cannulating delivery needle is sized as a 14-gauge needle to reduce deflection of the tip.

10. The apparatus of claim 9, wherein a distal most end of a tip of the cannulating delivery needle comprises a slot on one side of the cannula delivery needle for guiding deployment of the helical portion therefrom in a known direction and an extra coil of the helical portion of the coil electrode remains inside the cannulating delivery needle when the coil electrode is deployed in order to exert pressure against inner walls of the cannulating delivery needle to restrict rotation of the coil electrode when deployed.

11. The apparatus of claim 10, wherein the helical portion and the tip of the cannulating delivery needle have generally complementary cross sectional shapes in order to restrict rotation of the coil electrode during deployment.

12. The apparatus of claim 11, wherein the cross sectional shapes are selected from a circular segment, a triangle, a polygon, and a squircle.

13. The apparatus of claim 1, further comprising an introducer sheath sized and shaped to slidingly receive the cannulating delivery needle.

14. The apparatus of claim 13, wherein the cannulating delivery needle is sized as a 14-gauge needle and the introducer sheath is sized as a 12-gauge needle.

15. The apparatus of claim 14, wherein the introducer sheath comprises an electrically insulating outer layer.

16. The apparatus of claim 15, further comprising a trocar sized and shaped to be slidingly received within the introducer sheath.

17. The apparatus of claim 1, wherein the helical portion and the tip of the cannulating delivery needle have generally complementary cross sectional shapes being selected from a circular segment, a triangle, a polygon, and a squircle.

18. The apparatus of claim 1, wherein the first fin has a height at a portion thereof that is similar to a diameter of the handle.

19. The apparatus of claim 18, wherein the first fin has a curved first portion with an increasing height adjacent to the cannulating delivery needle and a tapered second portion adjacent to the first portion with a decreasing height.

* * * * *